United States Patent
Thenuwara et al.

(10) Patent No.: US 9,037,267 B2
(45) Date of Patent: May 19, 2015

(54) COCHLEAR LEAD

(75) Inventors: Chuladatta Thenuwara, Castaic, CA (US); Timothy Beerling, San Francisco, CA (US)

(73) Assignee: ADVANCED BIONICS LLC, Valencia, CA (US)

( * ) Notice: Subject to any disclaimer, the term of this patent is extended or adjusted under 35 U.S.C. 154(b) by 1087 days.

(21) Appl. No.: 12/789,264

(22) Filed: May 27, 2010

(65) Prior Publication Data

US 2011/0295352 A1    Dec. 1, 2011

(51) Int. Cl.
*A61N 1/05*    (2006.01)
*A61N 1/36*    (2006.01)

(52) U.S. Cl.
CPC ........... *A61N 1/0541* (2013.01); *A61N 1/36032* (2013.01)

(58) Field of Classification Search
CPC .................... A61N 1/0541; A61N 1/36032
USPC ........................................ 607/116, 136, 137
See application file for complete search history.

(56) References Cited

U.S. PATENT DOCUMENTS

| | | | |
|---|---|---|---|
| 4,284,085 A * | 8/1981 | Hansen et al. | 607/137 |
| 5,437,632 A | 8/1995 | Engelson | |
| 5,470,322 A | 11/1995 | Horzewski et al. | |
| 5,476,497 A | 12/1995 | Mower et al. | |
| 5,573,520 A | 11/1996 | Schwartz et al. | |
| 5,630,839 A | 5/1997 | Corbett et al. | |
| 5,653,742 A | 8/1997 | Parker et al. | |
| 5,762,630 A | 6/1998 | Bley et al. | |
| 5,800,500 A | 9/1998 | Spelman et al. | |
| 5,999,859 A | 12/1999 | Jolly | |
| 6,048,338 A | 4/2000 | Larson et al. | |
| 6,119,044 A | 9/2000 | Kuzma et al. | |
| 6,125,302 A | 9/2000 | Kuzma | |
| 6,321,125 B1 | 11/2001 | Kuzma | |
| 6,368,316 B1 | 4/2002 | Jansen et al. | |
| 6,421,569 B1 | 7/2002 | Treaba et al. | |
| 6,428,489 B1 | 8/2002 | Jacobsen et al. | |
| 6,475,209 B1 | 11/2002 | Larson et al. | |
| 6,556,873 B1 | 4/2003 | Smits | |
| 6,562,021 B1 | 5/2003 | Derbin et al. | |

(Continued)

FOREIGN PATENT DOCUMENTS

| | | |
|---|---|---|
| EP | 1341578 B1 | 4/2002 |
| EP | 2209520 A1 | 7/2003 |

(Continued)

OTHER PUBLICATIONS

He, Bo et al., Surface Texture effect on Friction of a Microtextured Polydimethylsiloxane, Tribology Letters, vol. 31, No. 3, Aug. 12, 2008; pp. 1-11.

(Continued)

*Primary Examiner* — Joseph Dietrich
(74) *Attorney, Agent, or Firm* — Steven L. Nichols; Van Cott, Bagley, Cornwall & McCarthy P.C.

(57) ABSTRACT

A cochlear lead includes a plurality of electrodes configured to stimulate an auditory nerve from within a cochlea and a flexible body supporting the plurality of electrodes along a length of the flexible body. A stiffening element is slidably encapsulated within the flexible body and positioned such that the stiffening element plastically deforms upon insertion into a curved portion of the cochlea.

27 Claims, 18 Drawing Sheets

(56) References Cited

U.S. PATENT DOCUMENTS

| | | |
|---|---|---|
| 6,604,283 B1 | 8/2003 | Kuzma |
| 6,757,970 B1 | 7/2004 | Kuzma et al. |
| 6,858,680 B2 | 2/2005 | Gunatillake et al. |
| 6,887,235 B2 | 5/2005 | O'Connor et al. |
| 6,968,238 B1 | 11/2005 | Kuzma |
| 6,999,821 B2 | 2/2006 | Jenney et al. |
| 7,047,081 B2 | 5/2006 | Kuzma |
| 7,050,858 B1 | 5/2006 | Kuzma et al. |
| 7,063,708 B2 | 6/2006 | Gibson et al. |
| 7,066,931 B2 | 6/2006 | O'Connor et al. |
| 7,115,183 B2 | 10/2006 | Larson et al. |
| 7,146,227 B2 | 12/2006 | Dadd et al. |
| 7,239,923 B1 | 7/2007 | Tockman et al. |
| 7,269,461 B2 | 9/2007 | Dadd et al. |
| 7,272,449 B2 | 9/2007 | Dadd et al. |
| 7,315,763 B2 | 1/2008 | Kuzma et al. |
| 7,319,906 B2 | 1/2008 | Kuzma et al. |
| 7,328,072 B2 | 2/2008 | Milojevic et al. |
| 7,389,148 B1 | 6/2008 | Morgan |
| 7,403,823 B1 | 7/2008 | Kroll et al. |
| 7,451,000 B2 | 11/2008 | Gibson et al. |
| 7,540,865 B2 | 6/2009 | Griffin et al. |
| 7,571,012 B2 | 8/2009 | Gibson |
| 7,742,827 B2 | 6/2010 | Lenarz et al. |
| 2002/0029074 A1 | 3/2002 | Treaba et al. |
| 2002/0161114 A1 | 10/2002 | Gunatillake et al. |
| 2003/0040684 A1 | 2/2003 | Soukup |
| 2003/0045921 A1 | 3/2003 | Dadd et al. |
| 2003/0093139 A1 | 5/2003 | Gibson et al. |
| 2003/0181967 A1 | 9/2003 | Dadd et al. |
| 2004/0030376 A1 | 2/2004 | Gibson et al. |
| 2004/0078057 A1 | 4/2004 | Gibson |
| 2004/0127968 A1 | 7/2004 | Kuzma et al. |
| 2005/0234535 A1 | 10/2005 | Risi et al. |
| 2006/0089569 A1 | 4/2006 | Soukup et al. |
| 2006/0235500 A1 | 10/2006 | Gibson et al. |
| 2006/0247749 A1 | 11/2006 | Colvin |
| 2007/0073130 A1 | 3/2007 | Finch et al. |
| 2007/0073371 A1 | 3/2007 | Dadd et al. |
| 2007/0127745 A1 | 6/2007 | Gibson et al. |
| 2007/0162098 A1 | 7/2007 | Risi et al. |
| 2008/0027527 A1 | 1/2008 | Kuzma et al. |
| 2008/0077049 A1 | 3/2008 | Hirshman |
| 2008/0109011 A1 | 5/2008 | Thenuwara et al. |
| 2008/0269864 A1 | 10/2008 | Dadd et al. |
| 2009/0030483 A1 | 1/2009 | Risi et al. |
| 2009/0043358 A1 | 2/2009 | Dadd et al. |
| 2009/0043369 A1 | 2/2009 | Radeloff |
| 2009/0043370 A1 | 2/2009 | Gibson et al. |
| 2009/0165921 A1 | 7/2009 | Kaiser |
| 2009/0312769 A1 | 12/2009 | Dadd et al. |
| 2010/0057180 A1 | 3/2010 | Gibson et al. |
| 2010/0106232 A1 | 4/2010 | Dadd et al. |
| 2010/0204768 A1 | 8/2010 | Jolly et al. |
| 2010/0287770 A1 | 11/2010 | Dadd et al. |
| 2011/0016710 A1 | 1/2011 | Dadd |
| 2011/0319907 A1 | 12/2011 | Gallegos et al. |
| 2012/0035615 A1 | 2/2012 | Koester et al. |

FOREIGN PATENT DOCUMENTS

| | | |
|---|---|---|
| EP | 1604626 A2 | 12/2005 |
| EP | 1604626 A3 | 12/2005 |
| EP | 1189560 B1 | 3/2006 |
| EP | 1604626 B1 | 12/2008 |
| EP | 2042137 A1 | 4/2009 |
| WO | 9306698 | 4/1993 |
| WO | 9710784 | 3/1997 |
| WO | 0071063 | 11/2000 |
| WO | 0228474 | 4/2001 |
| WO | 0228473 | 4/2002 |
| WO | 0230507 | 4/2002 |
| WO | 0232498 | 4/2002 |
| WO | 0243623 | 6/2002 |
| WO | 02094334 | 11/2002 |
| WO | 03049658 | 6/2003 |
| WO | 2004002570 | 1/2004 |
| WO | 2007002879 A1 | 3/2007 |
| WO | 2007027879 | 3/2007 |
| WO | 2009065127 A1 | 5/2009 |
| WO | 2009065171 A1 | 5/2009 |
| WO | 2009079704 A1 | 7/2009 |
| WO | 2010015016 A1 | 2/2010 |
| WO | 2010015017 A1 | 2/2010 |
| WO | 2010091237 A2 | 8/2010 |
| WO | 2010091237 A3 | 11/2010 |
| WO | 2011149695 A1 | 12/2011 |

OTHER PUBLICATIONS

Stover, Timo et al., "Microstructured Cochlear implant electrodes," Subproject T1 of Collaborative Research Center 599; pp. 1-2; Feb. 7, 2011.

Lenarz, Thomas et al., "Nerve-Electrode Interface," Subproject D2 of Collaborative Research Center 599; pp. 1-2; Feb. 7, 2011.

Reuter, G. et al., "Fine tuning of cochlear implant materials—cell interactions by femtosecond laser microstructuring." European Cells and Materials vol. 13. Suppl. 3, 2007 (p. 10).

Rebscher et al, Strategies to Improve Electrode Positioning and Safety in Cochlear Implants, IEEE Trans Biomed Eng, 46(3) 340-352, 1999.

Kha et al., Stiffness Properties of Nucleus Standard Straight and Contour Electrode Arrays, Med and Eng Phys 26 677-685, 2004.

\* cited by examiner

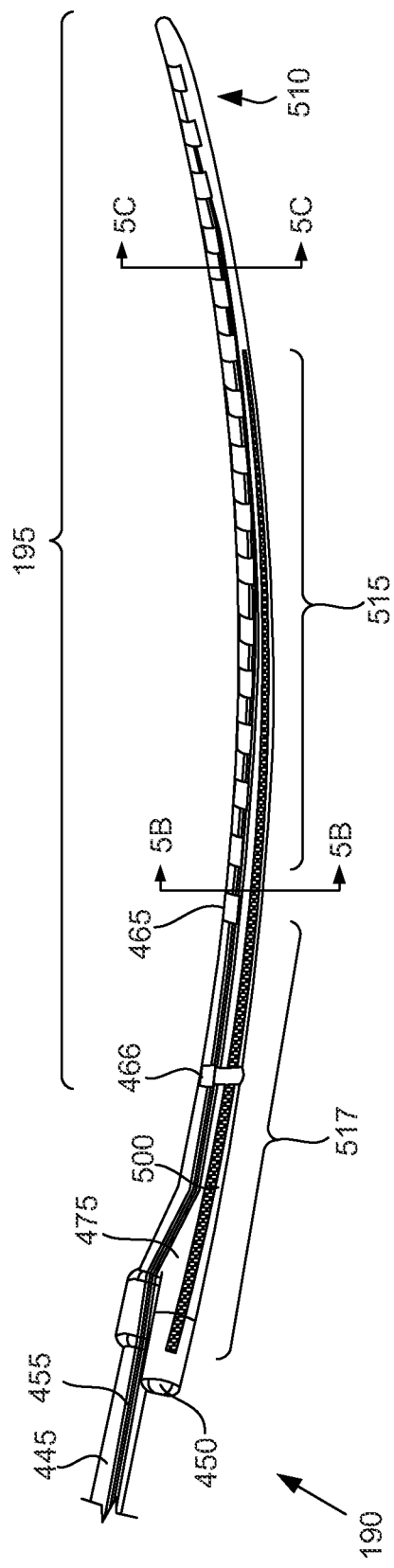
Fig. 5A
Fig. 5B
Fig. 5C

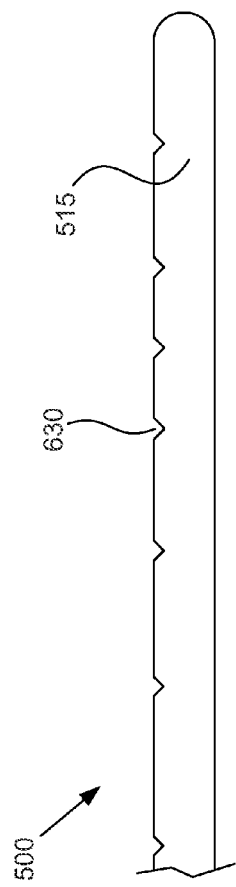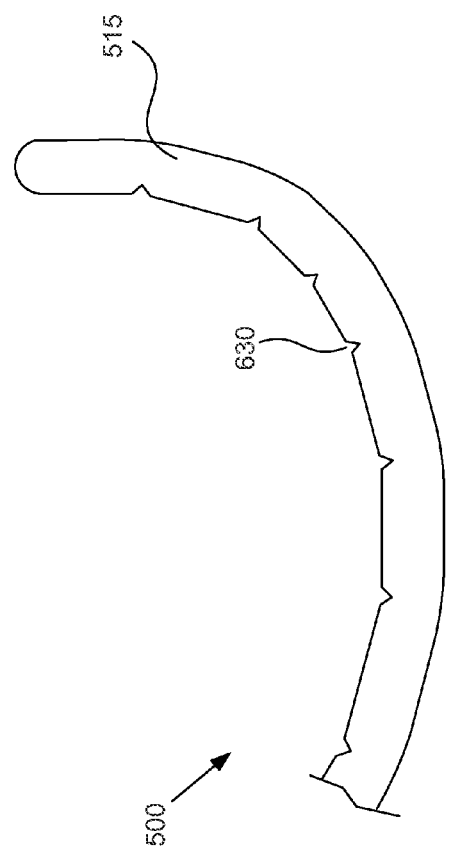

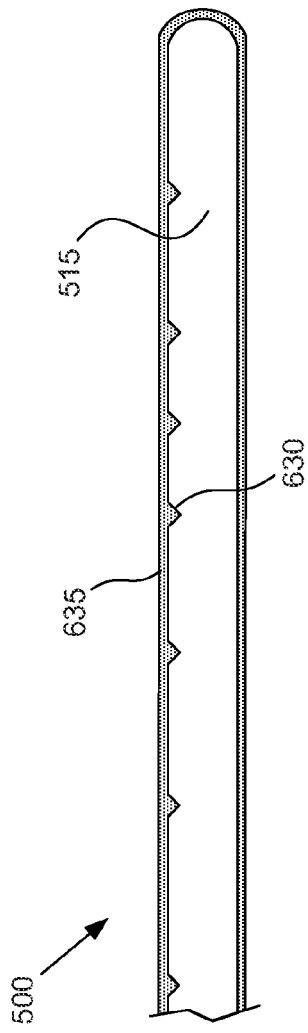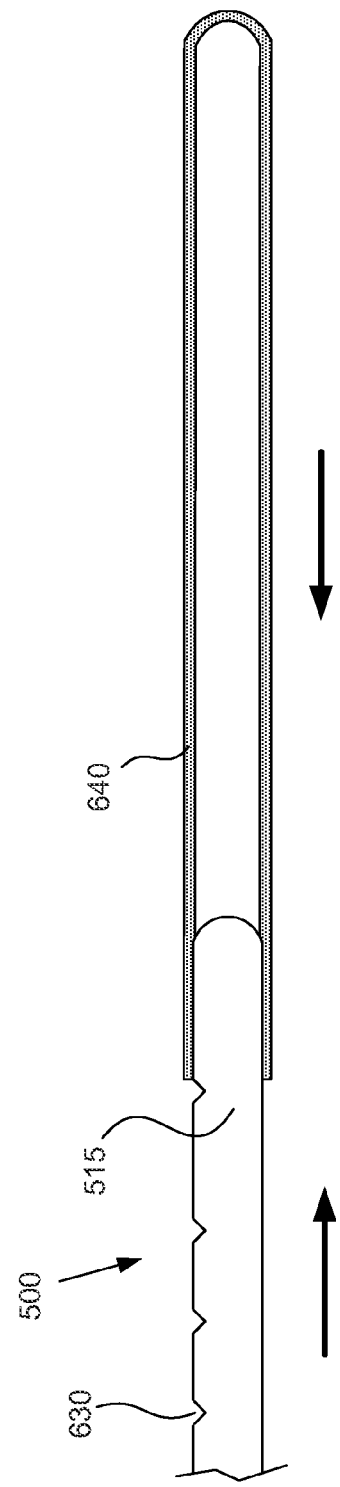

1100

```
┌─────────────────────────────────────────────────┐
│ Provide a plurality of electrodes and form the  │
│ electrodes into a first portion of the flexible │
│ body, the first portion of the flexible body    │
│ having a channel which runs down at least a     │
│ portion of its length.                          │
│ (step 1105)                                     │
└─────────────────────────────────────────────────┘
                         │
┌─────────────────────────────────────────────────┐
│ Alter geometry/anneal distal portion of         │
│ stiffening element.                             │
│ (step 1110)                                     │
└─────────────────────────────────────────────────┘
                         │
┌─────────────────────────────────────────────────┐
│ Coat the stiffening element with a thin layer   │
│ or place a sock over the stiffening element     │
│ (step 1115)                                     │
└─────────────────────────────────────────────────┘
                 ┌───────┴───────┐
┌────────────────────────┐  ┌────────────────────────┐
│ Place the stiffening   │  │ Form a lumen by placing│
│ element in the channel │  │ a removable core pin   │
│ and form a second      │  │ into the channel and   │
│ portion of the flexible│  │ forming a second       │
│ body to encapsulate    │  │ portion of the flexible│
│ the stiffening element.│  │ body around the core   │
│ (step 1120)            │  │ pin, then removing the │
│                        │  │ core pin.              │
│                        │  │ (step 1125)            │
└────────────────────────┘  └────────────────────────┘
                                      │
                            ┌────────────────────────┐
                            │ Put the stiffening     │
                            │ element into the lumen │
                            │ and seal the lumen to  │
                            │ encapsulate the        │
                            │ stiffening element.    │
                            │ (step 1130)            │
                            └────────────────────────┘
```

Insert the electrode array into a cochlea such that the stiffening element enters a curved portion of the cochlea, prevents the buckling of the cochlear lead, and redirects the axial insertion force into a tangential force.
(step 1205)

Continue to insert the electrode array into the cochlea such that the stiffening element extends at least to 180° and is plastically deformed in a shape which corresponds to the interior of the cochlea.
(step 1210)

*Fig. 12*

COCHLEAR LEAD

BACKGROUND

Hearing loss can be corrected using a number of approaches, including surgically placing a cochlear implant which includes a cochlear lead having an electrode array which is placed into the cochlea of the patient. The electrode array presents electrical stimulation directly to auditory nerve fibers in the cochlea. This leads to the perception of sound in the brain and provides at least partial restoration of hearing function. To minimize damage sensitive tissues within the patient's cochlea, it can be desirable for the electrode array to be accurately placed within the cochlea using a minimum amount of insertion force. After surgery, it is desirable that the electrode array remains in place within the cochlea. A variety of forces can tend to cause motion of the cochlear lead, including growth of the patient's head, participation in recreational activities, accidents, etc. If the electrode array shifts its position within the cochlea, the patient's sense of hearing can be compromised.

BRIEF DESCRIPTION OF THE DRAWINGS

The accompanying drawings illustrate various embodiments of the principles described herein and are a part of the specification. The illustrated embodiments are merely examples and do not limit the scope of the claims.

FIG. 5A is a partial side view of an illustrative cochlear lead, according to one embodiment of principles described herein.

FIG. 5B shows a cross-section of an illustrative cochlear lead, according to one embodiment of principles described herein.

FIG. 5C shows a cross-section of an illustrative cochlear lead, according to one embodiment of principles described herein.

FIG. 11 is a flowchart showing an illustrative method for forming a cochlear lead, according to one embodiment of principles described herein.

FIG. 12 is a flowchart showing an illustrative method for using a cochlear lead, according to one embodiment of principles described herein.

Throughout the drawings, identical reference numbers designate similar, but not necessarily identical, elements.

DETAILED DESCRIPTION

Figure 1:
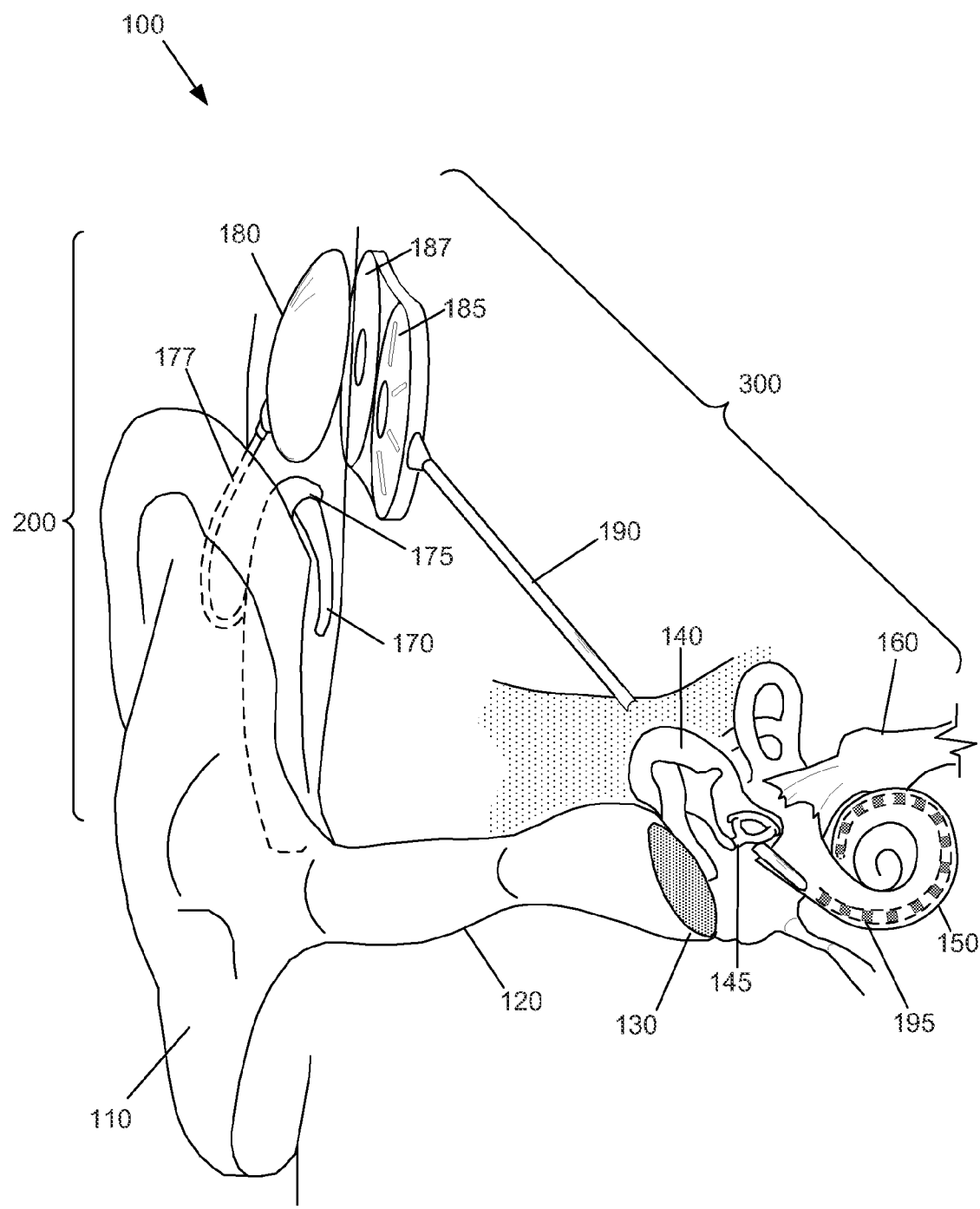
FIG. 1 is a diagram showing an illustrative cochlear implant system in use, according to one embodiment of principles described herein.

In human hearing, hair cells in the cochlea respond to sound waves and produce corresponding auditory nerve impulses. These nerve impulses are then conducted to the brain and perceived as sound.

Hearing loss, which may be due to many different causes, is generally of two types: conductive and sensorineural. Conductive hearing loss typically occurs where the normal mechanical pathways for sound to reach the hair cells in the cochlea are impeded, for example, from damage to the ossicles. Conductive hearing loss may often be helped by using conventional hearing aids that amplify sounds so that acoustic information can reach the cochlea and the hair cells. Some types of conductive hearing loss are also treatable by surgical procedures.

Many people who are profoundly deaf, however, have sensorineural hearing loss. This type of hearing loss can arise from the absence or the destruction of the hair cells in the cochlea which then no longer transduce acoustic signals into auditory nerve impulses. Individuals with sensorineural hearing loss may be unable to derive significant benefit from conventional hearing aid systems alone, no matter how loud the acoustic stimulus is. This is because the mechanism for transducing sound energy into auditory nerve impulses has been damaged. Thus, in the absence of properly functioning hair cells, auditory nerve impulses cannot be generated directly from sounds.

To overcome sensorineural deafness, cochlear implant systems, or cochlear prostheses, have been developed that can bypass the hair cells located in the cochlea by presenting electrical stimulation directly to the auditory nerve fibers. This leads to the perception of sound in the brain and provides at least partial restoration of hearing function. Most of these cochlear prosthesis systems treat sensorineural deficit by stimulating the ganglion cells in the cochlea directly using an implanted lead that has an electrode array. Thus, a cochlear prosthesis operates by directly stimulating the auditory nerve cells, bypassing the defective cochlear hair cells that normally transduce acoustic energy into electrical activity to the connected auditory nerve cells.

A cochlear implant system typically comprises both an external unit that receives and processes ambient sound waves and a cochlear implant that receives data from the external unit and uses that data to directly stimulate the auditory nerve. In a typical cochlear implant, a microphone receives sound and converts it into electrical signals. These electrical signals are transmitted to a processor implanted in the patient's body and connected to a lead having an electrode array implanted within one of the cochlear ducts, such as the scala tympani. The processor separates acoustic signals into a number of parallel channels of information, each representing a narrow band of frequencies within the perceived audio spectrum. Ideally, each channel of information should be conveyed selectively to a subset of auditory nerve cells that normally transmit information about that frequency band to the brain. Those nerve cells are arranged in an orderly tonotopic sequence, from the highest frequencies at the basal end of the cochlear spiral to progressively lower frequencies towards the apex. The processor then sends the appropriate channels of information to one or more of the electrode contacts, which then generate electrical fields which stimulate the desire subset of auditory nerve cells. This provides the patient with a sense of hearing:

To minimize damage to sensitive tissues within the patient's cochlea, it can be desirable for the cochlear implant to be accurately placed within the cochlea using a minimum amount of insertion force. The cochlear implant should be designed so that the insertion forces do not kink or otherwise damage the delicate wires and electrodes contained within the implant. After surgery, it is desirable that the cochlear implant remains in place within the cochlea. A variety of forces can tend to cause motion of the cochlear implant, including growth of the patient's head, repetitive motions such as chewing and yawning, participation in recreational activities, accidents, etc. If a cochlear implant shifts its position, the patient's sense of hearing can be compromised.

According to one illustrative embodiment, the portion of the lead that is inserted into the cochlea can be constructed from biocompatible silicone, platinum-iridium wires, and platinum electrodes. The portion of the lead to be inserted into the cochlea is designed to be relatively flexible so that it can curve around the helical interior of the cochlea. To provide the desired level of rigidity near the base of the lead, a stiffening element that is more rigid than the body of the cochlear lead is inserted into the basal portion of the lead. According to one illustrative embodiment, this stiffening element serves at least four purposes. First, the stiffening element provides additional rigidity in the basal portion of the lead, thereby reducing the likelihood that the insertion forces will kink the lead. Second, the stiffening element provides the surgeon with greater control over the placement of the lead within the cochlea. Third, the stiffening element redirects the insertion force into a tangential force, which allows the cochlear lead to be inserted deeper into the cochlea with less applied force. Fourth, at least a portion of the stiffening element may be formed from a material which plastically deforms during insertion, which allows the stiffening element to conform to the shape of the cochlea and prevents undesirable motion of the lead after insertion.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "an embodiment," "an example," or similar language means that a particular feature, structure, or characteristic described in connection with the embodiment or example is included in at least that one embodiment, but not necessarily in other embodiments. The various instances of the phrase "in one embodiment" or similar phrases in various places in the specification are not necessarily all referring to the same embodiment.

FIG. 1 is a diagram showing one illustrative embodiment of a cochlear implant system (100) having a cochlear implant (300) with an electrode array (195) that is surgically placed within the patient's cochlea. Ordinarily, sound enters the external ear, or pinna, (110) and is directed into the auditory canal (120) where the sound wave vibrates the tympanic membrane (130). The motion of the tympanic membrane is amplified and transmitted through the ossicular chain (140), which consists of three bones in the middle ear. The third bone of the ossicular chain (140), the stirrup (145), contacts the outer surface of the cochlea (150) and causes movement of the fluid within the cochlea. Cochlear hair cells respond to the fluid-borne vibration in the cochlea (150) and trigger neural electrical signals that are conducted from the cochlea to the auditory cortex by the auditory nerve (160).

As indicated above, the cochlear implant (300) is a surgically implanted electronic device that provides a sense of sound to a person who is profoundly deaf or severely hard of hearing. In many cases, deafness is caused by the absence or destruction of the hair cells in the cochlea, i.e., sensorineural hearing loss. In the absence of properly functioning hair cells, there is no way auditory nerve impulses can be directly generated from ambient sound. Thus, conventional hearing aids, which amplify external sound waves, provide no benefit to persons suffering from complete sensorineural hearing loss.

Unlike hearing aids, the cochlear implant (300) does not amplify sound, but works by directly stimulating any functioning auditory nerve cells inside the cochlea (150) with electrical impulses representing the ambient acoustic sound. Cochlear prosthesis typically involves the implantation of electrodes into the cochlea. The cochlear implant operates by direct electrical stimulation of the auditory nerve cells, bypassing the defective cochlear hair cells that normally transduce acoustic energy into electrical energy.

External components (200) of the cochlear implant system can include a Behind-The-Ear (BTE) unit (175), which contains the sound processor and has a microphone (170), a cable (177), and a transmitter (180). The microphone (170) picks up sound from the environment and converts it into electrical impulses. The sound processor within the BTE unit (175) selectively filters and manipulates the electrical impulses and sends the processed electrical signals through the cable (177) to the transmitter (180). The transmitter (180) receives the processed electrical signals from the processor and transmits them to the implanted antenna (187) by electromagnetic transmission. In some cochlear implant systems, the transmitter (180) is held in place by magnetic interaction with a magnet (189) in the underlying antenna (187).

The components of the cochlear implant (300) include an internal processor (185), an antenna (187), and a cochlear lead (190) having an electrode array (195). The internal processor (185) and antenna (187) are secured beneath the user's skin, typically above and behind the pinna (110). The antenna (187) receives signals and power from the transmitter (180). The internal processor (185) receives these signals and performs one or more operations on the signals to generate modified signals. These modified signals are then sent through the cochlear lead (190) to the electrode array (195), which is the portion of the cochlear lead (190) that is implanted within the cochlea (150) and provides electrical stimulation to the auditory nerve (160).

The cochlear implant (300) stimulates different portions of the cochlea (150) according to the frequencies detected by the microphone (170), just as a normal functioning ear would experience stimulation at different portions of the cochlea depending on the frequency of sound vibrating the liquid within the cochlea (150). This allows the brain to interpret the frequency of the sound as if the hair cells of the basilar membrane were functioning properly.

The cochlear lead typically comprises an electrode array that is implanted in the scala tympani. The electrode array typically includes several separately connected stimulating electrode contacts, conventionally numbering about 6 to 30, longitudinally disposed on a thin, elongated, flexible carrier. The electrode array is pushed into the scala tympani duct in the cochlea, typically to a depth of about 13 to 30 mm via a cochleostomy or via a surgical opening made in the round window at the basal end of the duct.

In use, the cochlear electrode array delivers electrical current into the fluids and tissues immediately surrounding the individual electrode contacts to create transient potential gradients that, if sufficiently strong, cause the nearby auditory nerve fibers to generate action potentials. The auditory nerve fibers branch from cell bodies located in the spiral ganglion, which lies in the modiolus, adjacent to the inside wall of the scala tympani. The density of electrical current flowing through volume conductors such as tissues and fluids tends to be highest near the electrode contact that is the source of such current. Consequently, stimulation at one contact site tends to selectively activate those spiral ganglion cells and their auditory nerve fibers that are closest to that contact site.

Figure 2:
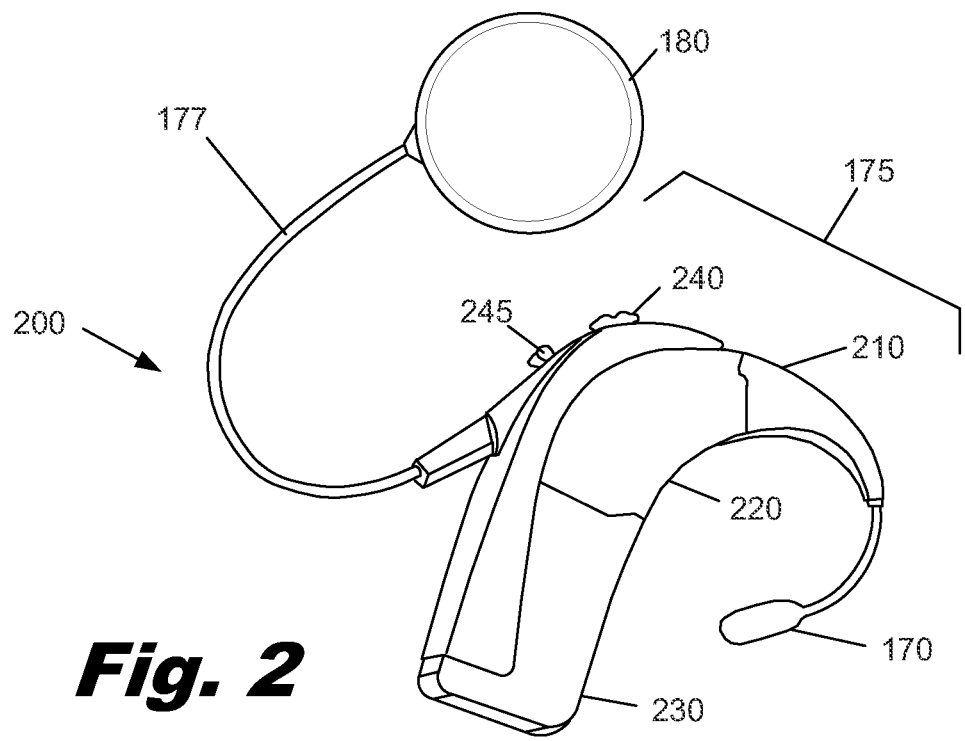
FIG. 2 is a diagram showing external components of an illustrative cochlear implant system, according to one embodiment of principles described herein.

FIG. 2 is an illustrative diagram showing a more detailed view of the external components (200) of one embodiment of a cochlear implant system. External components (200) of the cochlear implant system include a BTE unit (175), which comprises a microphone (170), an ear hook (210), a sound processor (220), and a battery (230), which may be rechargeable. The microphone (170) picks up sound from the environment and converts it into electrical impulses. The sound processor (220) selectively filters and manipulates the electrical impulses and sends the processed electrical signals through a cable (177) to the transmitter (180). A number of controls (240, 245) adjust the operation of the processor (220). These controls may include a volume switch (240) and program selection switch (245). The transmitter (180) receives the processed electrical signals from the processor (220) and transmits these electrical signals and power from the battery (230) to the cochlear implant by electromagnetic transmission.

Figure 3:
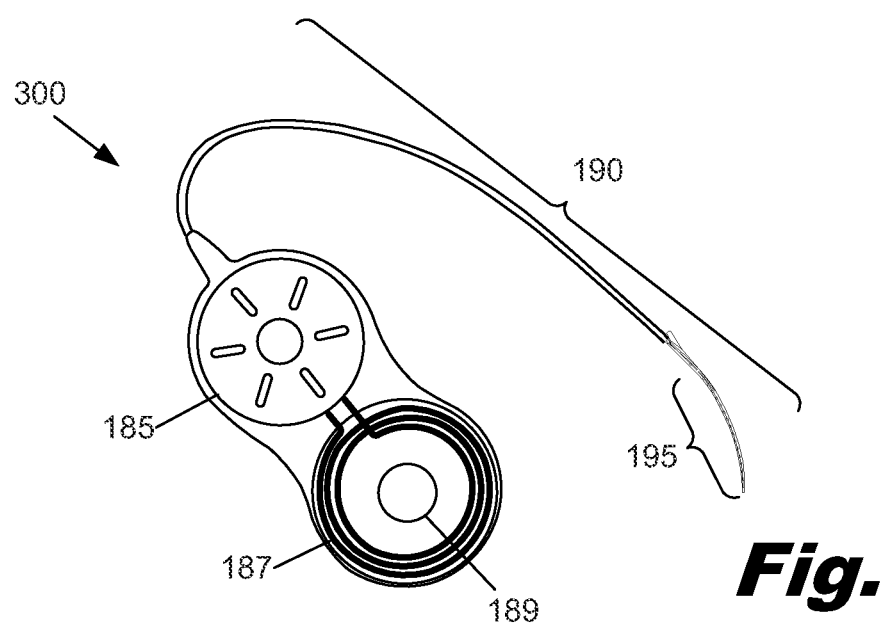
FIG. 3 is a diagram showing the internal components of an illustrative cochlear implant system, according to one embodiment of principles described herein.

FIG. 3 is an illustrative diagram showing one embodiment of a cochlear implant (300), including an internal processor (185), an antenna (187), and a cochlear lead (190) having an electrode array (195). The cochlear implant (300) is surgically implanted such that the electrode array (195) is internal to the cochlea, as shown in FIG. 1. The internal processor (185) and antenna (187) are secured beneath the user's skin, typically above and behind the pinna (110), with the cochlear lead (190) connecting the internal processor (185) to the electrode array (195) within the cochlea. According to one illustrative embodiment, the electrode array (195) is straight or slightly curved before being inserted into the cochlea (150. As discussed below, the electrode array (195) is designed for lateral wall placement within the cochlea (150). As discussed above, the antenna (187) receives signals from the transmitter (180) and sends the signals to the internal processor (185). The internal processor (185) modifies the signals and passes them through the cochlear lead (190) to the electrode array (195). The electrode array (195) is inserted into the cochlea and provides electrical stimulation to the auditory nerve. This provides the user with sensory input that is a representation of external sound waves sensed by the microphone (170).

Figure 4:
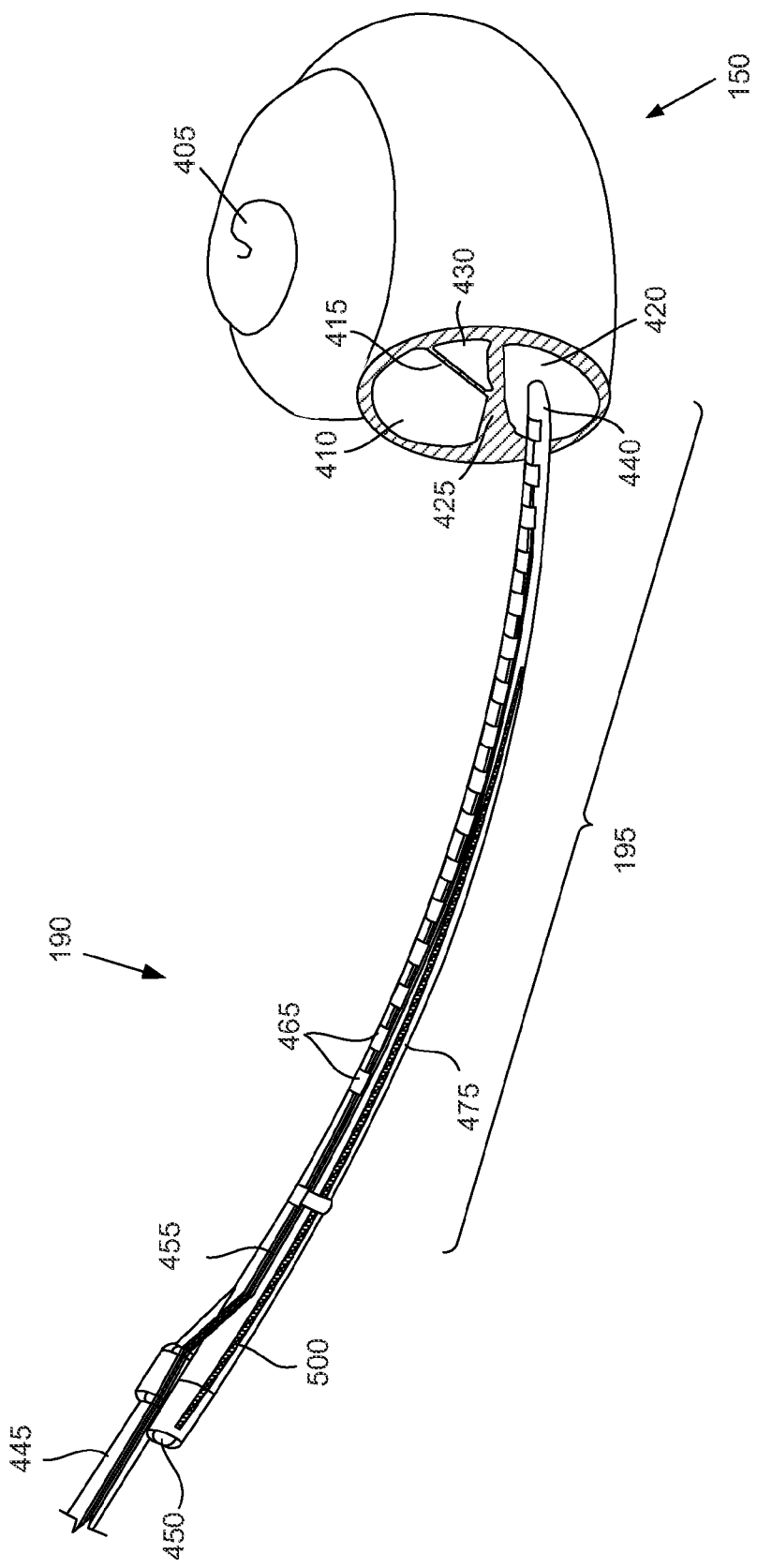
FIG. 4 is a cross-sectional view of a cochlea with an illustrative cochlear lead which includes an electrode array and stiffening element, according to one embodiment of principles described herein.

FIG. 4 is a partially cutaway perspective view of a cochlea (150) and shows an illustrative electrode array (195) being inserted into the cochlea (150). The primary structure of the cochlea is a hollow, helically coiled, tubular bone, similar to a nautilus shell. The coiled tube is divided through most of its length into three fluid-filled spaces (scalae). The scala vestibuli (410) is partitioned from the scala media (430) by Reissner's membrane (415) and lies superior to it. The scala tympani (420) is partitioned from the scala media (430) by the basilar membrane (425) and lies inferior to it. A typical human cochlea includes approximately two and a half helical turns of its constituent channels. The cochlear lead (190) is inserted into one of the scalae, typically the scala tympani (420), to bring the individual electrodes into close proximity with the tonotopically organized nerves.

The illustrative cochlear lead (190) includes a lead body (445). The lead body (445) connects the electrode array (195) to the internal processor (185, FIG. 3). A number of wires (455) pass through the lead body (445) to bring electrical signals from the internal processor (185, FIG. 3) to the electrode array (195). According to one illustrative embodiment, proximal of the electrode array (195) is a molded silicone rubber feature (450). The feature (450) can serve a variety of functions, including, but not limited to, providing a structure that can be gripped or pushed by an insertion tool and providing a visual indicator of how far the cochlear lead (190) has been inserted.

The wires (455) that conduct the electrical signals generated by the processor are connected to the electrodes (465) within the electrode array (195). For example, electrical signals which correspond to a low frequency sound may be communicated via a first wire to an electrode near the tip (440) of the electrode array (195). Electrical signals which correspond to a high frequency sound may be communicated by a second wire to an electrode (465) near the proximal end of the electrode array (195). According to one illustrative embodiment, there may be one wire (455) for each electrode (465) within the electrode array (195). The internal processor (185, FIG. 3) may then control the electrical field generated by each electrode individually. For example, one electrode may be designated as a ground electrode. The remainder of the electrodes may then generate electrical fields which correspond to various frequencies of sound. Additionally or alternatively, adjacent electrodes may be paired, with one electrode serving as a ground and the other electrode being actively driven to produce the desired electrical field.

According to one illustrative embodiment, the wires (455) and portions of the electrodes (465) are encased in a flexible body (475). The flexible body (475) may be formed from a variety of biocompatible materials, including, but not limited to, medical grade silicone rubber. The flexible body (475) secures and protects the wires (455) and electrodes (465). The flexible body (475) allows the electrode array (195) to bend and conform to the geometry of the cochlea. When placed within the cochlea (150), the electrode array (195) is positioned adjacent the lateral or outside wall of the scala tympani (420) and brings the individual electrodes into close proximity with the tonotopically organized nerves in the cochlea (150).

Additionally, as can be seen in FIG. 4, and described further in FIG. 5, a stiffening element (500) may be included in a proximal region of the flexible body (475) of the cochlear lead (190) through the molded silicone rubber feature (450). As previously mentioned, the stiffening element (500) allows the cochlear lead to be more precisely positioned within the cochlea and reduces the propensity of the cochlear lead (190) to kink. In embodiments where the stiffening element (500) is plastically deformable, the stiffening element (500) conforms to the curvature of the cochlea during insertion. This can help prevent undesirable motion of the lead within the cochlea. The stiffening element and its function are described in more detail below.

FIG. 5A is a partial side view of an illustrative cochlear lead (190). The cochlear lead (190) includes an electrode array (195) comprising electrodes (465), a lead body (445) carrying wires (455) that extend from the internal processor (185, FIG. 3) to the electrodes (465), a flexible body (475) on which electrodes (465) are disposed, a stiffening element (500) disposed within a portion of the flexible body (475), and a molded silicone rubber feature (450) proximal of the electrode array (195). The illustrative cochlear lead (190) further includes a cochleostomy marker (466) as a guide for positioning the electrode array (195). When the electrode array (195) is properly positioned within the cochlea, the cochleostomy marker (466) is positioned at or near the cochleostomy, and, the electrodes (465) are well positioned to stimulate the tonotopically-arranged groups of nerve endings.

The stiffening element (500) may be located within the flexible body (475) and extend from at or near the molded feature (450) to a location within the electrode array (195). The stiffening element (500) makes the proximal region of the electrode array stiffer, or more rigid, than the distal end (510). According to one embodiment, the stiffening element (500) comprises or consists essentially of platinum. In other embodiments, it may be made of any material which provides the desired mechanical and chemical properties. These properties may include low yield strength and chemical inertness. By way of example and not limitation, the stiffening element (500) may be a plastic, metal, glass, composite, or other material. According to one illustrative embodiment, the stiffening element (500) may comprise or consist of gold or a gold alloy.

According to one embodiment, stiffening element (500) extends approximately 8 to 14 mm from the cochleostomy. For example, the stiffening element may extend into the cochlea approximately 8.0 mm to 9.0 mm from cochleostomy. In this illustrative embodiment; the stiffening element (500) extends from the molded rubber feature (450) through the electrode array to approximately the sixth or seventh electrode from the tip of the electrode array (195). However, the actual position of the stiffening element (500) within the cochlear lead (190) is dependent on a number of factors including length of the electrode array, the spacing of the electrodes, the number of electrodes, the planned insertion depth of the electrode array and other factors. The stiffening element (500) is divided into to two portions, a proximal portion (517) and a distal portion (515).

FIG. 5B shows a cross-section along line 5B-5B of a portion of the illustrative cochlear lead (190) in which the stiffening element (500) is disposed. The wires (455) may be shaped into a wire bundle by the electrode (465). Portions of the electrode, the wires, and the stiffening element (500) are encapsulated by the flexible body (475). In this particular embodiment, the electrodes (465) are disposed within the flexible body (475) on the medial wall of the electrode array. The stiffening element (500) is disposed in flexible body (475) opposite the electrodes (465).

FIG. 5C is a cross-sectional diagram along line 5C-5C in the distal end (510) of the cochlear lead (190). In this illustrative embodiment, the electrode (465) has a lower profile and contains a reduced number of wires (455) than that shown in FIG. 5B. The stiffening element (500) does not extend into the distal end (510) of the cochlear lead (190). As shown in the present embodiment, the distal end (510) of the cochlear lead (190) may be flattened, thinned, or the shape or dimensions otherwise modified to allow it to be more flexible in the direction of the curvature of the cochlea than the rest of the lead. This may, in combination with the stiffening element (500) reduce the frictional forces between the distal end (510) and the cochlea in order to help prevent the lead from damaging the cochlea. The entire length of the distal end (510) may be flattened or altered, according to one embodiment, or only the distal most tip (440) of the distal end (510) may be flattened or altered, according to another embodiment.

The electrodes (465) within the flattened portion of the lead may be appropriately sized so as to fit and function effectively within the reduced cross-section. Additionally, any other components within the flattened or size-reduced portion of the lead can be appropriately sized to fit within the cross-section.

Figure 6A:
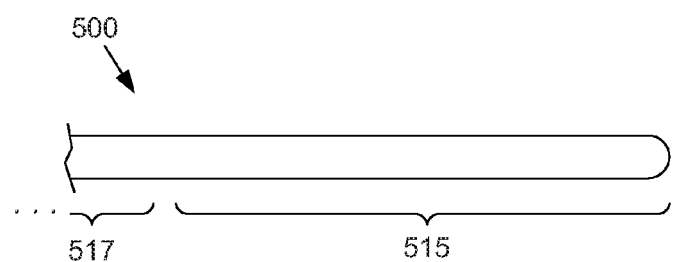
FIGS. 6A-6P show diagrams of distal portions of illustrative stiffening elements, according various embodiments of principles described herein.

FIGS. 6A-6P show various embodiments of the illustrative distal portion (515) of the stiffening element (500). The distal portion (515) may be from 2 to 6 millimeters long, according to some embodiments. For example, it has been found that a distal portion (515) with a length between 5 to 6 millimeters may be desirable. The distal portion (515) may be longer in other embodiments, as desired. It may be desirable for the distal portion of the stiffening element to have different material properties than the rest of the stiffening element. For example, the distal portion of the stiffening element may be plastically deformed during the insertion of the cochlear lead into the cochlea. As used in the specification and appended claims, the term "plastic deformation" refers to non-reversible deformation of a solid body due to applied forces. In contrast, elastic deformation is a reversible deformation of solid body due to applied forces.

The stiffness and ductility of the distal portion (515) of the stiffening element (500) could significantly influence the amount of force required to insert the electrode array (195) into the cochlea. For example, a distal portion (515) with a relatively high stiffness could require a greater insertion force to insert the electrode array (195) into the cochlea. Additionally, the properties of the distal portion (515) could influence the stability of the electrode array within the cochlea. For example, a distal portion (515) with high yield strength of 185 to 205 MPa may be more susceptible to migrate out from the cochlea due to strain energy. Conversely, a distal portion with a lower yield strength of 14 to 35 MPa may plastically conform to the shape of the cochlea and have a tendency to retain the electrode array in the cochlea.

In embodiments where the stiffening element is a metal, the distal portion (515) may be annealed. Annealing is a versatile heat treating process which alters the material properties (such as yield strength and ductility) of a metal. For example, annealing may be used to produce a distal portion having greater ductility and lower stiffness than the rest of the body (600) of the stiffening element (500). As will be described in further detail below, annealing the distal portion (515) may allow the distal portion (515) to maintain its bent shape after insertion into the cochlea. A variety of other techniques, such as work hardening, could be used to modify the yield strength, malleability, ductility, stiffness, or other characteristics of the stiffening element (500).

Figure 6B:
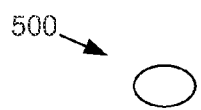
Figure 6C:
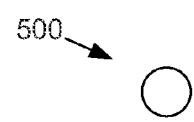

Additionally or alternatively, the geometry of the distal portion (515) can be altered to create the desired mechanical properties. FIGS. 6A-6P show illustrative embodiments of tip geometries that may be used. FIG. 6A shows a stiffening element (500) with a uniform cross section along its length. The stiffening element (500) is divided into two sections, a proximal portion (517) and a distal portion (515). As shown in the end views FIGS. 6B and 6C, the stiffening element (500) may have a variety of cross sectional geometries, including elliptical or circular. These cross sections can be selected to produce the desired stiffness. As discussed above, the distal portion (515) may also be annealed to modify its malleability, ductility, stiffness, or other characteristics.

Figure 6D:
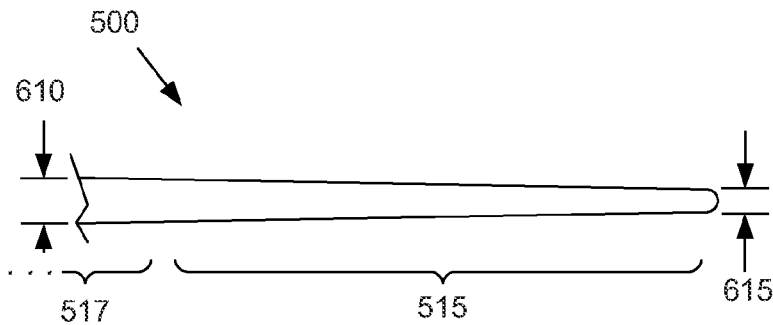

FIG. 6D is diagram of a stiffening element (500) in which the distal end (515) of the stiffening element has a smaller diameter or width (615) than the larger diameter (610) of proximal portion (517) of the stiffening element (500). The distal portion (515) may have a tapered geometry, shown as in the embodiment of FIG. 6D. The tapered geometry can be formed such that the distal portion (515) has a variety of cross sectional shapes as shown in the end views of FIGS. 6E-6H. Each end view shows an outline (620) of the profile of the proximal portion (517) and an outline (625) of the end of the distal portion (517).

Figure 6E:
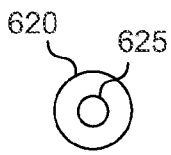

FIG. 6E shows an end view with concentric circles (620, 625), the outer circle (620) representing the cross sectional shape of proximal end (517) and the smaller circle (625) representing the cross sectional shape the end of the distal portion (515). Thus the combination of FIG. 6D and FIG. 6E shows that the distal portion (515) has a progressively reduced diameter along the length of the stiffening element (500).

Figure 6F:
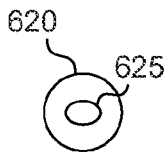
Figure 6G:
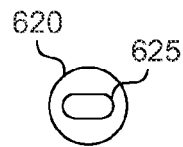
Figure 6H:
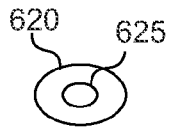

FIG. 6F shows an end view where the taper of the distal portion originates from a circular cross section (620) of the proximal portion (517) and is reduced into a smaller elliptical cross section (625) at the end of the distal portion (515). FIG. 6G shows a similar end view in which the distal portion (515) is flattened from a round cross section (620) into the flattened oblong cross section (625). FIG. 6H shows an end view of a taper which begins at larger elliptical cross section (620) and ends in a smaller elliptical cross section (625).

Figure 6I:
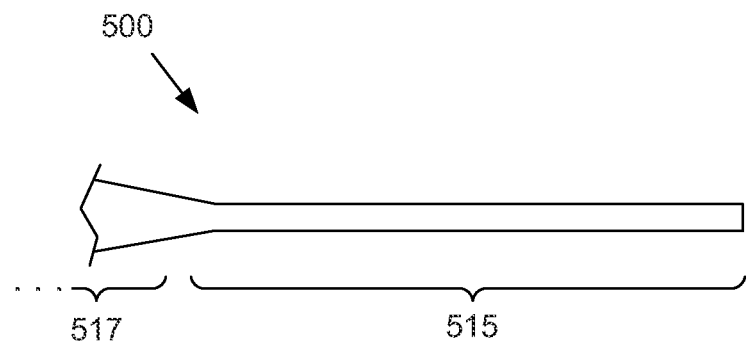
Figure 6J:
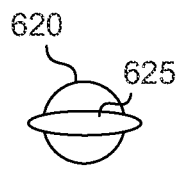
Figure 6K:
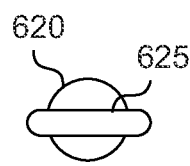
Figure 6L:
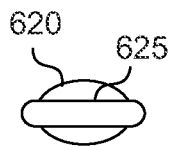

FIG. 6I is stiffening element (500) with a flattened distal portion (515). The distal portion (515) can be reduced in diameter or flattened using a variety of methods, including grinding, rolling, pressing, drawing, or other suitable technique. FIG. 6J shows an end view of the flattened taper which begins at a circular cross section (620) of the proximal portion (517) and is flattened to an elliptical cross section (625). Similarly, FIG. 6K is an end view of the flattened taper which begins at a circular cross section (620) and is flattened into an oval cross section (625). FIG. 6L is an end view of a flattened taper which begins in an elliptical cross section (620) and terminates in a flattened oval (625). The embodiments shown are only illustrative examples. A variety of other geometries could be used. For example, if the distal end (515) is ground into a particular shape, the flattened profile (625) may not be wider than the proximal portion (517).

FIG. 6M shows one illustrative embodiment of a distal portion (515) of a stiffening element (500) that has a number of micromachined features (630) disposed along one or more sides of the distal portion (515). For example, these features may be grooves which are orthogonal to the primary axis of the distal portion. According to one illustrative embodiment, these features are configured to facilitate bending of the stiffening element in one or more directions. The size and/or spacing of the features can produce variable bending along the length of the distal portion as shown in FIG. 6N. Portions of the distal portion that have larger or more closely spaced features (630) will have a lower bending stiffness and tendency for greater angular deflection. The micromachined distal portion (515) illustrated in FIGS. 6M and 6N may be directly disposed within the flexible body (475, FIG. 4) or may be coated with an additional thin layer of material as will be described below before forming it within the flexible body. The illustrative modifications shown in FIGS. 6M-6N to the distal portion of the stiffening element (500) reduce its bending stiffness in the direction of curvature of the electrode array (195) as it is inserted into the cochlea.

FIG. 6O is a cross sectional diagram of a distal portion (515) of an illustrative stiffening element (500). As described above, the distal portion (515) of the stiffening element (500) may include a number of micromachined features (630). In this illustrative embodiment, the stiffening element (500) is overcoated with a thin layer (635). This thin layer (635) may be formed from a number of materials and applied in a variety of ways. For example, the micromachined distal portion (515) may be coated with a thin layer of medical grade silicone rubber. The silicone rubber may fill the micromachined features (630) to prevent undesirable voids. This silicone coated stiffening element (500) can then be slidably encapsulated in a lumen. For example, the lumen may be lined with polytetrafluoroethylene (PTFE) or other friction reducing material.

In other embodiments, the thin layer (635) may be PTFE or other suitable polymer coating. The thin layer (635) may be deposited in a variety of ways including, dipping, brushing, spraying, or other methods. Following deposition of the thin layer (635), the coating may be cured or undergo other post deposition processing. The stiffening element (500) may then be formed into the flexible body. The thin layer (635) of PTFE on the outer surface of the stiffening element (500) may be configured to ensure that the medical grade silicone which makes up the flexible body of the electrode does not adhere to the stiffening element, allowing the stiffening element (500) to move within the flexible body (475, FIG. 5) as the electrode array (195, FIG. 5) bends during insertion into the cochlea. By allowing the relative motion of the stiffening element (500) and the flexible body (475, FIG. 5) during bending, the overall bending stiffness of the cochlear lead (190) is reduced while still maintaining its resistance to kinking.

FIG. 6P is a cross sectional diagram of a sock (640) which is placed over the stiffening element (500). According to one illustrative embodiment, the sock (640) may be formed from PTFE or other polymer. For example, the sock (640) may be formed from expanded PTFE. Expanded PTFE has high strength, chemical inertness, and a much lower modulus of elasticity than unexpanded PTFE. According to one illustrative embodiment, the expanded PTFE sock or liner may be a tube with an inside diameter of 0.006 inches and an outside diameter of 0.007 inches. Additionally, the size and shape of the sock (640) may be selected to allow more or less relative motion between the stiffening element (500) and the sock and between the sock and the flexible body (475). For example, in some embodiments, the sock (640) may be sized to fit relatively loosely over the stiffening element (500). This will allow the stiffening element (500) to slide within the sock (640) relatively easily. Alternatively, the sock (640) may be sized to fit more tightly around the stiffening element (500). In this embodiment, there may be little or no relative motion of the stiffening element (500) within the sock (640). Instead, the relative motion of the stiffening element (500) with respect to the flexible body (475, FIG. 5) may take place primarily at the interface between the outer surface of the sock (640) and the inner surface of the flexible body.

In some embodiments, the fit of the sock (640) over the stiffening element may vary from location to location. For example, the sock (640) may be formed so that it fits relatively snuggly over the stiffening element (500) near its proximal and distal ends, but have a looser fit in other locations. Additionally, the sock (640) may cover the entire stiffening element (500) or only a portion of the stiffening element (500). For example, the sock (640) may cover only the distal portion (515) of the stiffening element. Although the sock (640) is shown with an open end and a closed end, the sock may have both ends open or both ends closed.

Figure 7A:
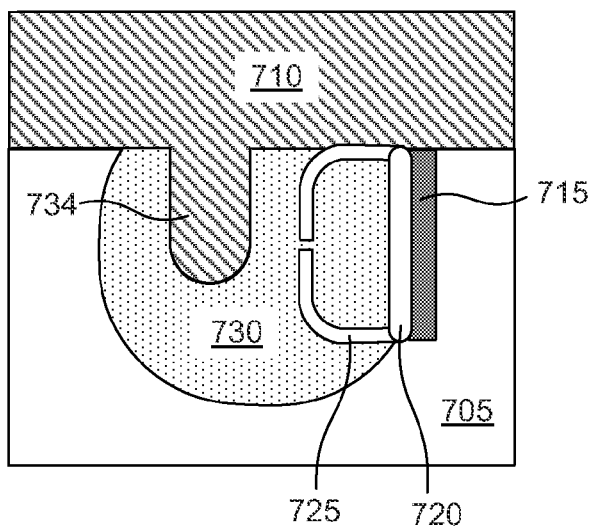
FIGS. 7A-7C are cross sectional diagrams of steps in an illustrative molding process for making a cochlear lead with an integral stiffening element, according to one embodiment of principles described herein.
Figure 7B:
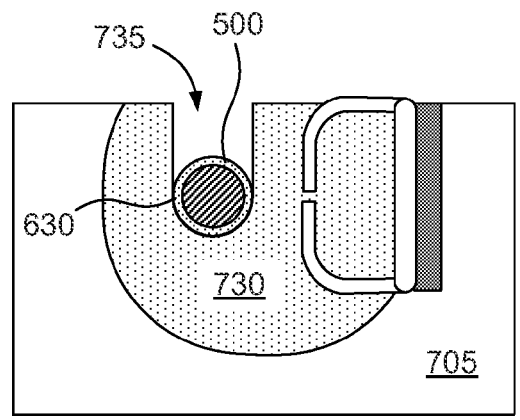
Figure 7C:
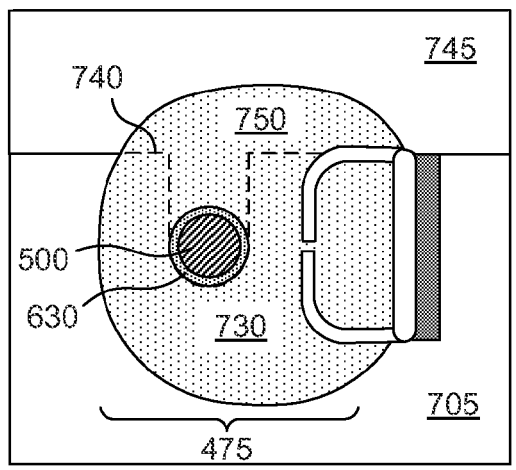

FIGS. 7A-7C are cross sectional diagrams of various illustrative steps in a process for forming a stiffening element (500) into a cochlear lead (190; FIG. 5). In one embodiment, the cochlear lead includes a number of electrodes (720) which have wings (725) which extend into the interior of the cochlear lead. These wings (725) form an enclosed space through which the wires (455, FIG. 5B) pass. During manufacturing, the electrodes (720) are attached to a sacrificial iron strip (715). The sacrificial iron strip holds the electrodes in place during the various manufacturing and molding steps used to form the cochlear lead. After the electrodes are molded into place, the sacrificial strip (715) can be removed.

In FIG. 7A, the sacrificial iron strip (715) and the electrodes (720) attached to the iron strip (715) are placed in the cavity of an insert mold bottom (705) and covered with a mold top (710). According to one illustrative embodiment, the mold top (710) includes a protrusion (734) which extends downward into the cavity formed by the bottom shell (705). Medical grade silicone is then injected to fill the cavity and surround the electrode wings (725). The medical grade silicone contacts the back and side portions of the electrode (720), but not the surface of the electrode that is joined to the sacrificial iron strip (715). The medical grade silicone is then cured to form a first portion (730) of the flexible body (475). The mold top (710) is then removed.

FIG. 7B is a cross sectional diagram of the cured first portion (730) of the flexible body, which includes a channel (735) formed by protrusion (734). The stiffening element (500) is placed in the bottom of the channel (735). In this illustrative embodiment, the stiffening element (500) is covered by a thin layer (635, FIG. 6F) and/or sock (640, FIG. 6G). As discussed above, the thin layer (635) and/or sock (640) may allow for differential motion between the stiffening element (500) and the flexible body.

After placing the stiffening element (500) in the bottom of the channel (735), a second mold top (745) may be placed over the first portion (730) of the flexible body and more medical grade silicone can be injected into the resulting cavity to fill the channel (735). This second portion (750) of the medical grade silicone is cured to complete the flexible body and encapsulate the stiffening element (500). A dotted line (740) shows the interface between the first and second portions (730, 750) which form the flexible body (475). The flexible body (475) is then removed from the mold.

Figure 8A:
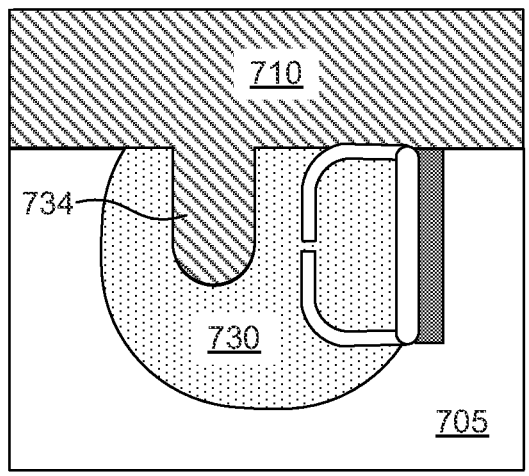
FIGS. 8A-8D are cross sectional diagrams of steps in an illustrative molding process for making a cochlear lead with an integral stiffening element, according to one embodiment of principles described herein.
Figure 8B:
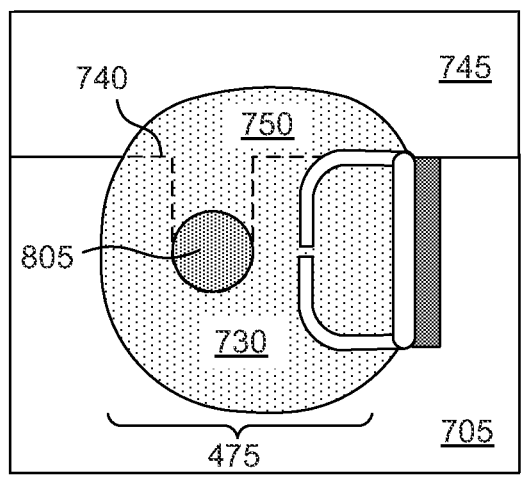

FIGS. 8A and 8B are cross sectional diagrams of illustrative steps of another method used to encapsulate a stiffening element (500) in the flexible body (475) of the cochlear lead (190). FIG. 8A shows the mold bottom and top (705, 710), which are similar to that illustrated in FIG. 7A. The mold bottom (705) contains the electrodes, and the mold top (710) fits over the mold bottom (705) to form a cavity into which medical grade silicone is injected. The mold top (710) includes a protrusion (734) that forms a channel (735) in the cured first portion (730) of silicone.

FIG. 8B illustrates using a core pin (805) to form a lumen in the flexible body (475). The core pin (805) may take a variety of forms including a PTFE monofilament or other fluorinated polymer element or a metal pin sprayed with mold release or coated with a fluoropolymer so that silicone does not substantially adhere to it. This allows the core pin (805) to be more easily removed from the flexible body (475). The removable metal or polymer core pin (805) may be covered with a fluoropolymer sleeve that remains in the flexible body after removal of the core pin (805).

Figure 8C:
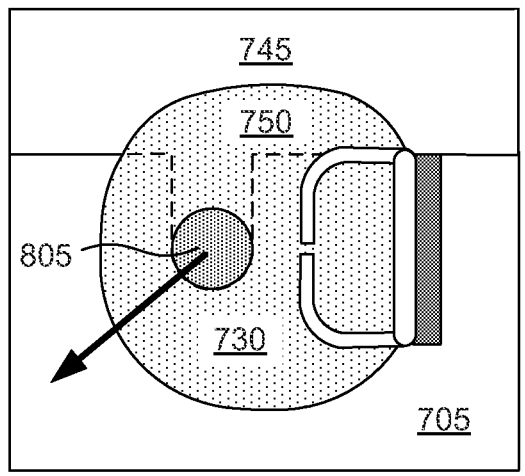
Figure 8D:
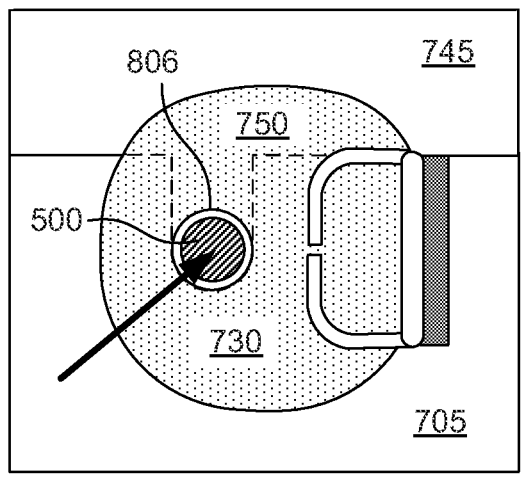

FIG. 8C illustrates the removal of the core pin (805) from the flexible body (475), creating a lumen. FIG. 8D illustrates the placement of the stiffening element (500) in the lumen (806). The stiffening element (500) may or may not fill the entire lumen (806). For example, where differential motion between the stiffening element and the flexible body are desired, the stiffening element (500) may have a relatively loose fit. Further, the stiffening element (500) may be any of the designs discussed above, including stiffening elements which are coated to reduce friction between the stiffening element and the surrounding silicone. After the insertion of the stiffening element, the lumen (806) is sealed with silicone to encapsulate the stiffening element within the flexible body.

Figure 9:
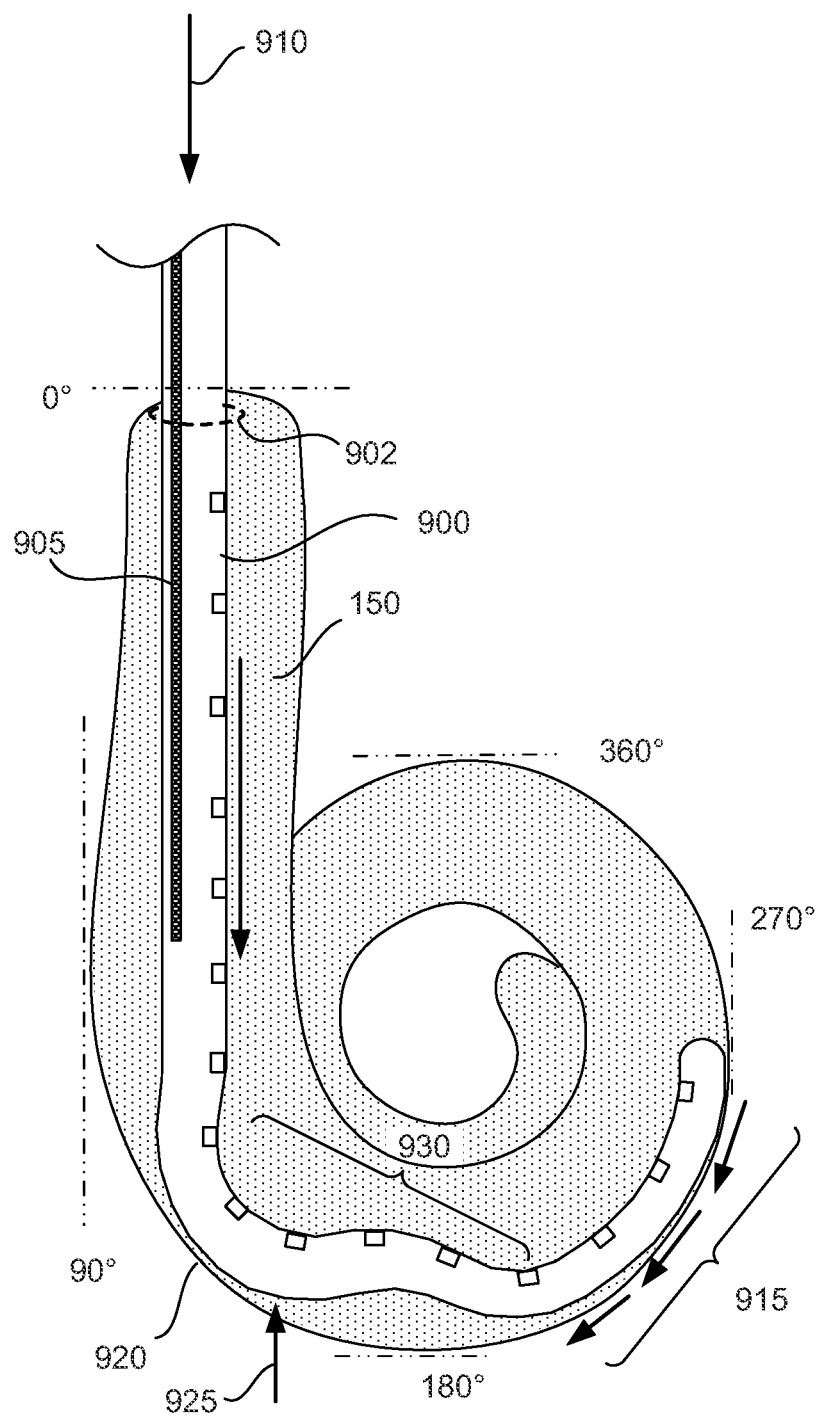
FIG. 9 is a cutaway view of a cochlea with a cochlear lead with a short stiffening element being inserted into the cochlea, according to one embodiment of principles described herein.
Figure 10A:
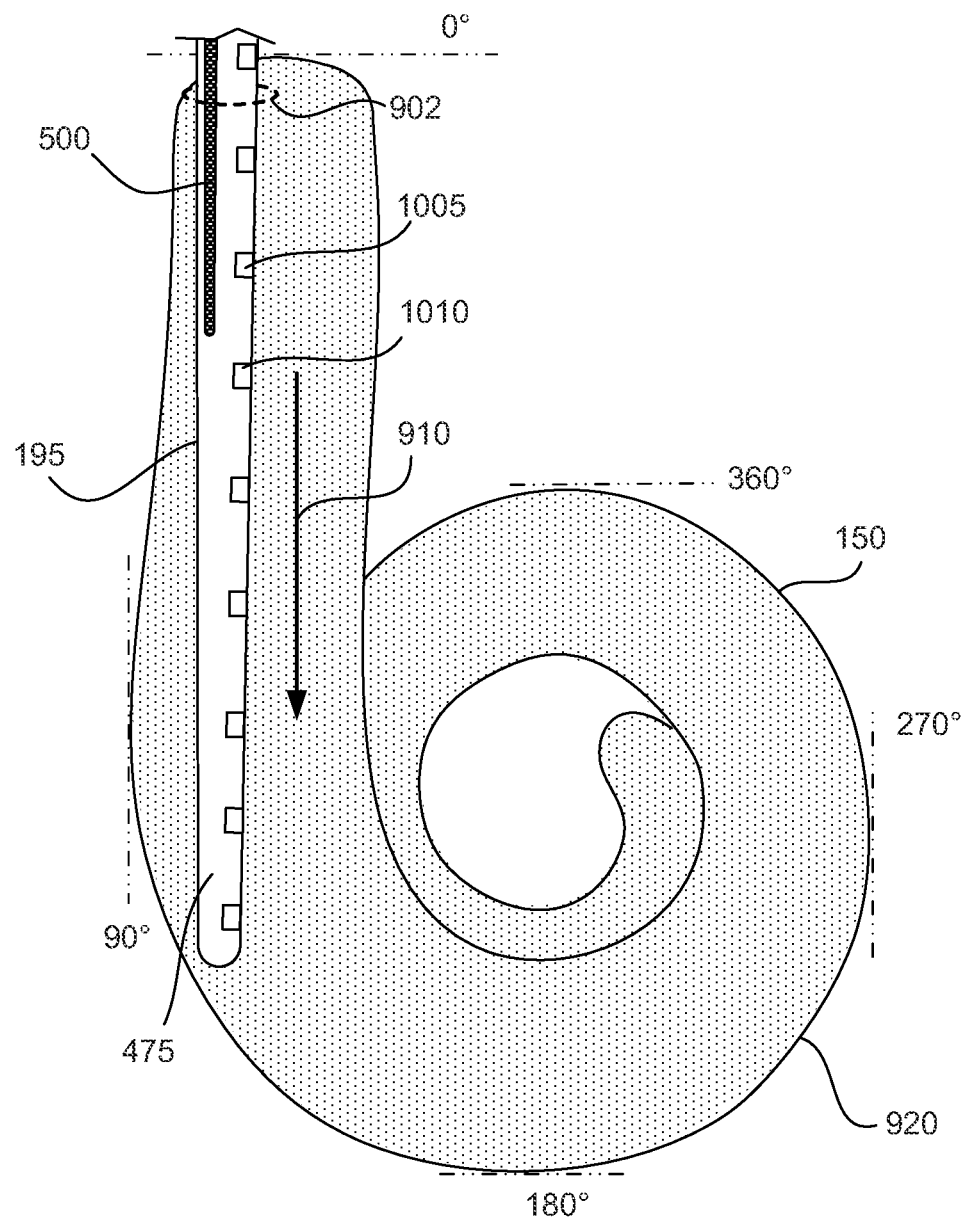
FIGS. 10A-10C are diagrams illustrating the insertion of an electrode array into a cochlea, according to one embodiment of principles described herein.
Figure 10B:
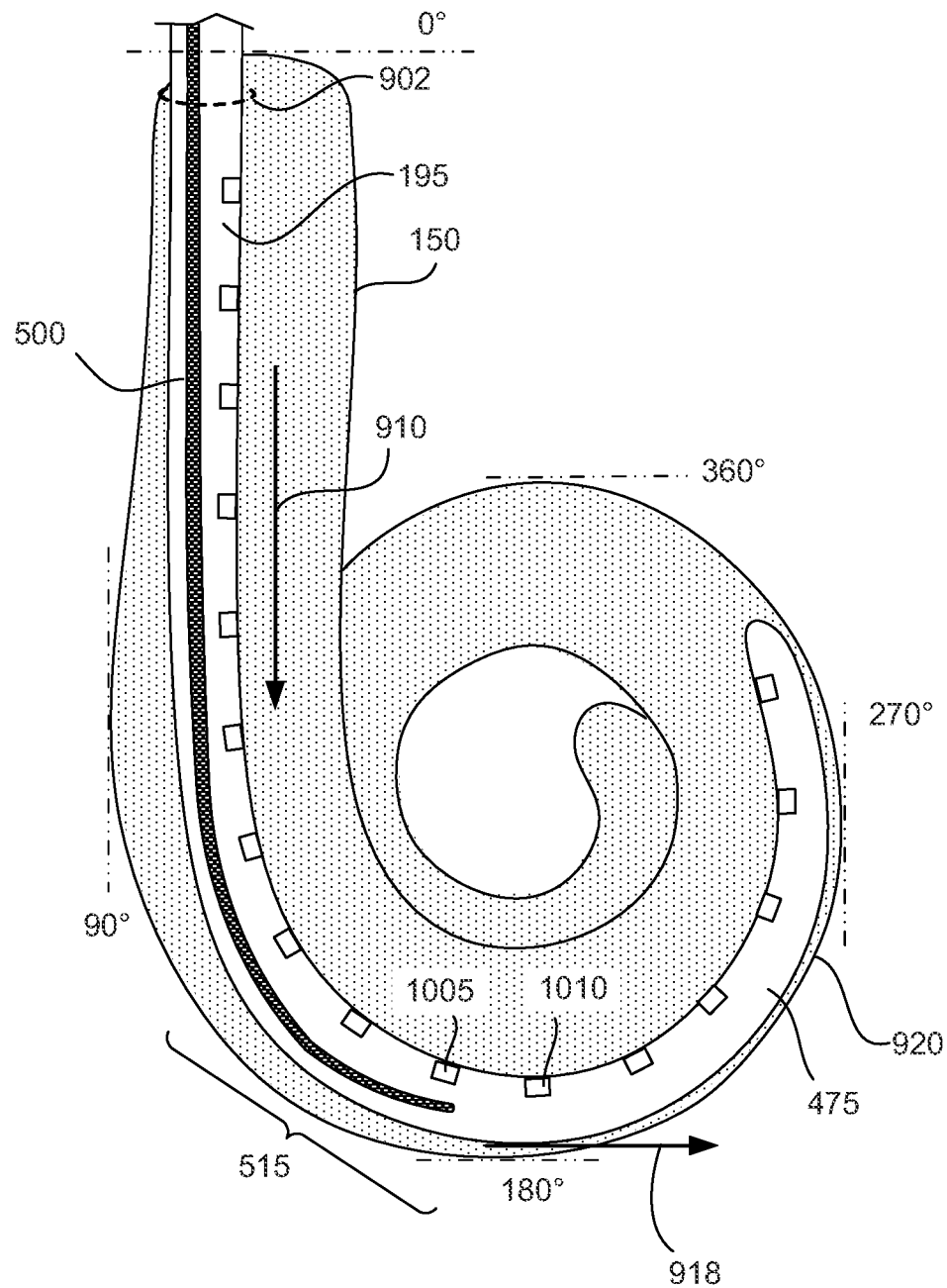
Figure 10C:
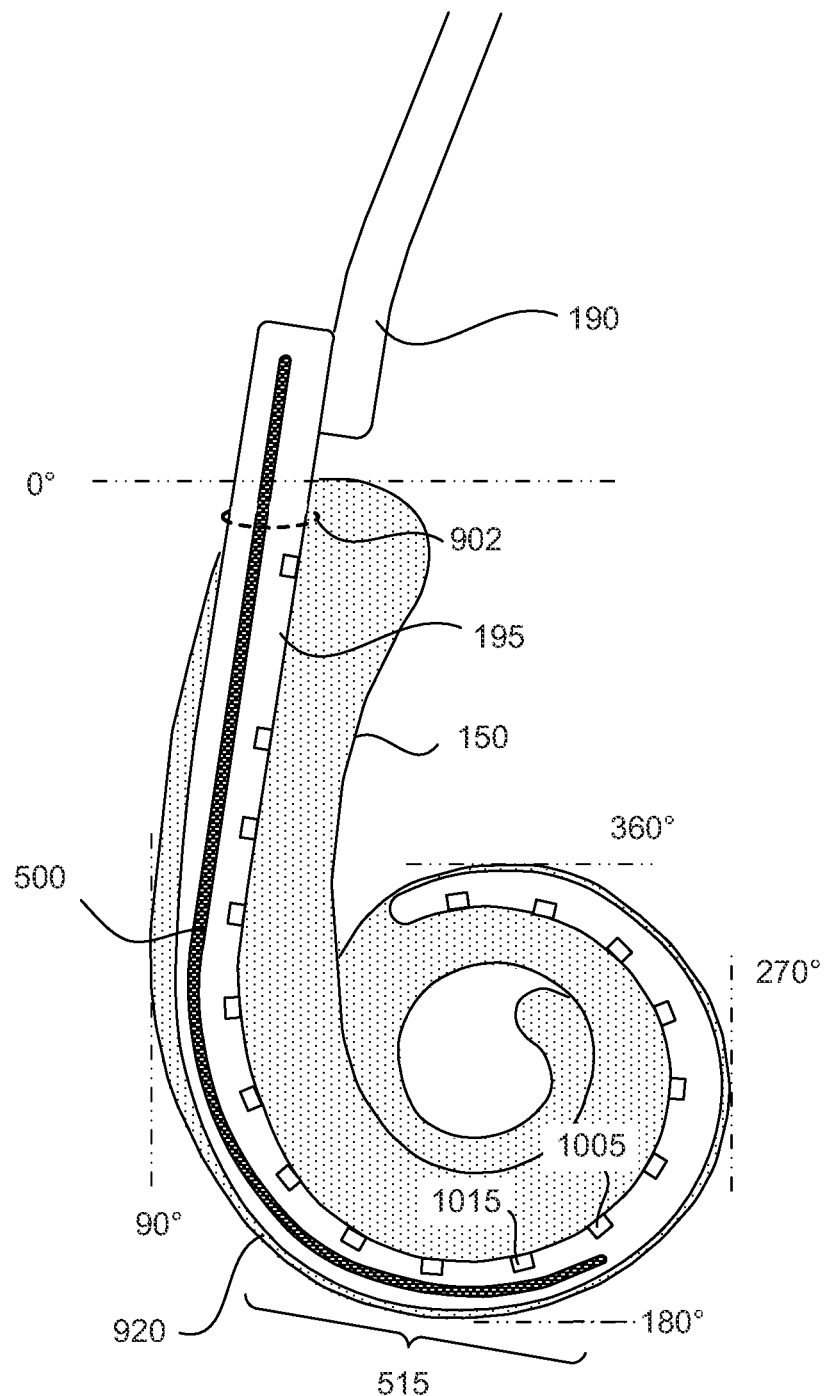

FIG. 9 is a cutaway view of a cochlea illustrating challenges in inserting a cochlear lead with a short stiffening element into a cochlea. FIGS. 10A-10C show an illustrative cochlear lead with a longer stiffening element than illustrated in FIG. 9. By contrasting the cochlear lead with a short stiffening element shown in FIG. 9 with the cochlear lead with a longer stiffening element shown in FIGS. 10A-10C, the advantages of the longer stiffening element can be more fully appreciated.

FIG. 9 shows an electrode array (900) of a cochlear lead with a short stiffening element (905) being inserted into a cochlea (150), illustrating the various forces acting on the electrode array (900) and kinking that may occur during insertion. The cochlear lead is designed such that the short stiffening element (905) extends only into the relatively straight portion of the cochlea (150), even when the electrode array (900) is fully inserted. The electrode array (900) is inserted into the cochlea (150) through a cochleostomy (902) by an axial insertion force (910). As the interior of the cochlea (150) curves, the axial insertion force (910) tends to push the electrode array (900) into an outer wall (920) of the cochlea (150). This can result in damage to the cochlea (150) and can ultimately lead to hearing loss that may otherwise be preventable.

A variety of techniques can be used to measure and communicate the insertion depth of an electrode array (900) into a cochlea (150). One technique describes cochlear locations and insertion depths using the angles of lines that are tangent to the wall (920) of the cochlea. According to one illustrative embodiment, a tangent line at the insertion point or cochleostomy (902) of the electrode array (900) is assigned an angle of 0° and serves as a reference point for measuring other angles. For example, other bench mark angles may be 90°, 180°, 270°, and 360°. These angles are illustrated in the figures as tangential broken lines and are labeled with the appropriate angle.

As the electrode array (900) is inserted, the frictional forces (915) between the surfaces of the electrode array (900) and the lateral wall (920) increase. While the short stiffening element (905) is useful in transmitting the axial insertion force (910) to the portion of the lead body in which it is located, buckling can occur in portions of the electrode array (900) distal of the short stiffening element (905).

It has been found from bone insertion studies that at an insertion depth of approximately 270 degrees, the frictional forces (915) can become great enough to prevent the further insertion of the electrode array (900). The continued exertion of the axial insertion force (910) can result in a combination of the frictional forces (915) and a vertical reaction force (925) that produces a buckling region (930). At this point, continuing to push the electrode array (900) into the cochlea (150) will probably not increase the insertion depth. Instead, continued axial force on the cochlear lead may cause further kinking/buckling of the electrode array (900). This can cause damage to the components of the electrode array and increase the trauma of sensitive tissues within the cochlea (150).

For full spectrum stimulation of the cochlea, it is desirable that the tip of the electrode array have an insertion depth of approximately 360° or more. This can place the electrodes of the electrode array into proximity with a significant portion of the tonotopically organized nerve endings in the cochlea.

FIG. 10A is a cutaway view that shows an illustrative electrode array (195) of a cochlear lead that has a longer stiffening element (500) than that illustrated in FIG. 9. This longer stiffening element (500) is configured to extend into the curved portions of the cochlea (150). According to one illustrative embodiment, the longer stiffening element (500) may be configured to slide within the flexible body (475) when the electrode array (195) is inserted into the cochlea (150). However, as illustrated in FIG. 10A during the initial insertion past the 90 degree point, the electrode array remains relatively straight. At this point in the insertion, the tip of the stiffening element (500) is located midway between sixth electrode (1010) and the seventh electrode (1005). According to one illustrative embodiment, the stiffening element (500) terminates approximately 11 to 12 millimeters from the distal tip of the electrode array (195).

FIG. 10B is a cutaway view which shows the illustrative electrode array (195) of FIG. 10A, of a cochlear lead having a longer stiffening element (500) than that of FIG. 9, which is inserted into the cochlea (150) past the 270 degree point. When the electrode array (195) is inserted such that the stiffening element (500) approaches the first turn in the cochlea (150), the stiffening element (500) begins to bend within the electrode array (195) as it conforms to the shape of the cochlea (150). As the stiffening element (500) bends within the electrode array (195), at least some of the axial insertion force (910) applied to the electrode array (195) is converted to a tangential force (918) in the direction of the distal portion (515) of the stiffening element (500). This may allow the electrode array (195) to be inserted deeper into the cochlea (150) with less insertion force (910) than would otherwise be required without the stiffening element (500). As a result; the electrode array (195) of a cochlear lead having the longer stiffening element (500) is able to be inserted to a depth beyond 270 degrees with reduced trauma to the cochlea (150).

In FIG. 10B, the tip of the electrode array (195) has been inserted slightly past 270° and the distal portion (515) of the stiffening element (500) is at approximately 180°. Because the stiffening element (500) extends into the first curve of the cochlea, buckling of the electrode array (195) during insertion is prevented. The buckling of the electrode array (195) may be reduced or prevented for at least two reasons. First, the stiffening element (500) imparts a higher stiffness to the portions of the electrode array in which it is located. Second, the stiffening element (500) redirects the insertion force from a vertical direction to a tangential direction, which reduces the frictional forces resisting the insertion of the electrode array (195). Converting the axial insertion force (910) to a tangential force (918) may allow the electrode array (195) to overcome the frictional forces between the cochlea (150) and electrode array (195), allow the electrode array (195) to be inserted farther into the cochlea (150), and lower the probability of damaging the cochlea (150) upon insertion.

As illustrated in FIG. 10B, the distal end of the stiffening element (500) has moved relative to the electrodes so that it is closer to the seventh electrode (1005). As discussed above, the stiffening element (500) is located in the part of the cochlear lead that will be implanted facing the lateral wall (920) of the cochlea. Consequently, as the electrode array bends to follow the curve of the cochlea (150), the stiffening element (500) has greater radius of curvature than the medial side of the cochlear lead. This results in a tendency for the tip of stiffening element (500) to slide within the flexible body (475). In embodiments where the stiffening element (500) is adhered to the flexible body (475), this can create additional bending stiffness which resists the bending during the insertion. However, in embodiments where the stiffening element (500) is free to move with respect to the flexible body (475), the overall bending stiffness of the electrode array (195) may be decreased while maintaining the desired resistance to kinking.

FIG. 10C is a cross sectional diagram that shows one illustrative embodiment of a cochlear lead (190) having a longer stiffening element (500), with the electrode array (195) in its final position within the cochlea (150). In the final position, the tip of the electrode array (195) may extend slightly past 360°, and the distal end of the stiffening element (500) may extend slightly past 180°. The position illustrated in FIG. 10C is only one illustrative configuration of an inserted electrode array (195). The electrode array (195) may be inserted more or less than shown in the figures.

As discussed above, the distal portion (515) of the stiffening element (500) can be annealed to produce a more compliant and malleable metal. Consequently, the distal portion (515) of the stiffening element (500) maintains its a shape after it is initially bent. This prevents the electrode array (195) from backing out of the cochlea (150) due to small external forces or to forces due to jostling, repetitive movements, or other movements. FIG. 10C shows that the electrode array (195) may be positioned adjacent the lateral, or outside, wall of the cochlea (150).

As mentioned previously, the distal portion (515) of the stiffening element (500) may be flattened, tapered, or otherwise reduced in diameter compared to rest of the stiffening element (500), in addition to possibly being annealed. Flattening or tapering the distal portion (515) may reduce the forces to the outer wall (920) of the cochlea (150). This may also allow the distal portion (515) to conform to the shape of the interior of the cochlea (150) more easily, while still being stiff enough to prevent buckling and maintain its plastic deformation after full insertion. According to one illustrative embodiment, the stiffening element (500) is positioned such that when the electrode array (195) is fully inserted into the cochlea (190) as shown in FIG. 10C, the stiffening element extends approximately 8 to 14 millimeters into the cochlea (190) as measured from the cochleostomy (902). In some embodiments, the stiffening element (500) may extend from 8 to 9 millimeters into the cochlea (150) when the electrode array (195) is fully inserted.

The additional insertion and bending of the electrode array (195) has also resulted in further motion of the tip of the stiffening element (500). In FIG. 100, the distal end of the stiffening element (500) is now between the seventh electrode (1005) and the eighth electrode (1015).

FIG. 11 is a flowchart (1100) of an illustrative method for forming a cochlear lead for insertion deeper into a cochlea. The method includes providing a plurality of electrodes and forming the electrodes into a first portion of a flexible body (step 1105). This first portion of the flexible body also contains a groove or channel which runs down at least a portion of its length.

The distal portion of a stiffening element may be geometrically altered or annealed (step 1110). As discussed above, annealing the distal portion may cause the properties of a metal stiffening element to change. By way of example and not limitation, the stiffness, strength, and malleability of the metal may be altered. For example, in some embodiments, it may be advantageous to anneal the distal portion of the stiffening element so that it is softer and more malleable than the body portion of the stiffening element. The distal portion may also be flattened in order to make the distal portion more flexible than the body of the stiffening element. The distal portion may be any length, though in some embodiments, the distal portion has a length from 2 mm to 6 mm. The stiffening element may have a variety of cross-sectional geometries, including round, oval, flat, rectangular, and other shapes. Additionally, the cross-section of the stiffening element may vary along its length. According to one illustrative embodiment, the stiffening element is constructed from platinum and has a diameter from 0.08 mm to 0.15 mm.

As discussed above, in some embodiments the stiffening element may also be coated with a thin layer (625, FIG. 6F) or a sock (630; FIG. 6G) may be placed over the stiffening element (step 1115). This thin layer or sock allows for the relative motion of the stiffening element with respect to the flexible body. The thin layer or sock does not necessarily cover the entire stiffening element. In some embodiments, the thin layer or sock may be selectively placed over portions of the stiffening element. According to one illustrative embodiment, the stiffening element (500) is placed in the channel and a second portion of the flexible body is formed which encapsulates the stiffening element in the first and second portions of the flexible body (step 1120).

Alternatively, a lumen may be formed by encapsulating a removable core pin, such as a PTFE rod, and forming the second portion of the flexible body around the PTFE rod such that the PTFE rod is encapsulated in the flexible body (step 1125). After curing the silicone which makes up the flexible body, the PTFE rod is removed.

The resulting cavity in the flexible body is a lumen into which the stiffening element is inserted (step 1130). As discussed above, the stiffening element may have a variety of configurations. For example, the stiffening element may or may not be coated with a thin layer or include a sock. The stiffening element may be appropriately sized so that it has the desired amount of contact and friction with the interior surfaces of the lumen. The stiffening element is then permanently encapsulated within the lumen by sealing the open end of the lumen.

The steps given above are only one illustrative embodiment of a method for forming a cochlear lead for insertion deeper into a cochlea. In alternative embodiments, steps could be added, omitted, or reordered. For example, in step 1110 and step 1115, the stiffening element is annealed and coated. However, these steps could just as easily be performed prior to the formation of the first portion of the flexible body as described in step 1105. Additionally, in some embodiments, the stiffening element may not be coated or placed in a sock as described in step 1115.

FIG. 12 is a flow chart (1200) which describes the insertion of an electrode array of a cochlear lead with a malleable stiffening element into a cochlea. This malleable stiffening element may also have a relatively low yield strength and/or low modulus of elasticity. The electrode array is inserted into a cochlea such that the stiffening element enters a curved portion of the cochlea, prevents buckling of the electrode array during insertion, and redirects the axial insertion into a tangential force (step 1205).

The insertion of the electrode array continues such that the stiffening element extends to at least the 180° and is plastically deformed in the shape of the interior of the electrode array (step 1210). The stiffening element is permanently deformed in the shape of the interior of the cochlear space in which it is inserted.

When a withdrawing force is applied, the permanently deformed shape of the stiffening element resists, but does not prevent, the withdrawal of the cochlear lead. This helps to reduce the likelihood of the lead backing out of the cochlea due to accidental forces, but still permits the surgical withdrawal of the electrode array if necessary.

The preceding description has been presented only to illustrate and describe embodiments and examples of the principles described. This description is not intended to be exhaustive or to limit these principles to any precise form disclosed. Many modifications and variations are possible in light of the above teaching.

What is claimed is:

1. A cochlear lead comprising:
 a plurality of electrodes configured to stimulate an auditory nerve from within a cochlea;
 a flexible body supporting the plurality of electrodes along a length of the flexible body; and
 a stiffening element slidably encapsulated within the flexible body and positioned such that the stiffening element plastically deforms upon insertion into a curved portion of the cochlea.

2. The cochlear lead of claim 1, in which a distal portion of the stiffening element is less stiff than a proximal portion of the stiffening element.

3. The cochlear lead of claim 2, in which the distal portion of the stiffening element is annealed.

4. The cochlear lead of claim 2, in which the distal portion of the stiffening element is annealed and the proximal portion is not annealed.

5. The cochlear lead of claim 2, in which both the distal and proximal portions of the stiffening element are annealed; a geometry of the distal portion being altered such that the distal portion is less stiff than the proximal portion of the stiffening element.

6. The cochlear lead of claim 2, in which the proximal portion of the stiffening element has a circular cross section having a diameter between 0.08 millimeters and 0.15 millimeters.

7. The cochlear lead of claim 2, in which the distal portion of the stiffening element has a length of approximately 2 to 6 millimeters.

8. The cochlear lead of claim 1, in which a distal portion of the stiffening element is flattened, such that the distal portion is more flexible in at least one direction of curvature than a body of the stiffening element.

9. The cochlear lead of claim 1, in which a distal portion of the stiffening element is tapered, such that the distal portion is more flexible than a body of the stiffening element.

10. The cochlear lead of claim 1, in which the stiffening element further comprises micromachined features configured to facilitate bending of the stiffening element, the micromachined features being disposed along one or more sides of the distal portion.

11. The cochlear lead of claim 10, in which the micromachined features comprise a series of notches disposed on a side of the stiffening element with a smaller radius of curvature when inserted into the cochlea.

12. The cochlear lead of claim 1, in which the stiffening element substantially comprises platinum.

13. The cochlear lead of claim 1, in which the stiffening element is positioned such that when the cochlear lead is fully inserted in the cochlea, the stiffening element extends approximately 8 to 14 millimeters into the cochlea as measured from a cochleostomy.

14. The cochlear lead of claim 1, in which the stiffening element is positioned such that when the cochlear lead is fully inserted in the cochlea, the stiffening element extends approximately 8 to 9 millimeters into the cochlea as measured from a cochleostomy.

15. The cochlear lead of claim 1, in which the stiffening element terminates approximately 11 to 12 millimeters from the distal tip of the cochlear lead.

16. The cochlear lead of claim 1, in which the stiffening element is coated with material configured to reduce adhesion between the stiffening element and the flexible body.

17. The cochlear lead of claim 1, further comprising a sock, the sock fitting over at least a portion of the stiffening element, the sock being configured to allow the stiffening element to slide relative to the flexible body when the cochlear lead bends during insertion into a cochlea.

18. The cochlear lead of claim 1, further comprising a closed lumen, the stiffening element being encapsulated within the lumen such that the stiffening element can slide relative to the flexible body when the cochlear lead bends during insertion into a cochlea.

19. The cochlear lead of claim 1, in which the stiffening element is configured to resist withdrawal of the cochlear lead away from the cochlea.

20. The cochlear lead of claim 1, in which the cochlear lead and slidably encapsulated stiffening element are configured to take a lateral position against an outside wall of a cochlear duct after insertion.

21. A method for forming a cochlear lead comprises:
providing a plurality of electrodes and forming the electrodes into a first portion of a flexible body, the first portion of the flexible body comprising a channel that runs down at least a portion of its length;
annealing a distal portion of a stiffening element; and
encapsulating the stiffening element in the flexible body such that the stiffening element is slidably disposed within the flexible body.

22. The method of claim 21, further comprising coating the stiffening element with a thin layer to reduce sliding resistance of the stiffening element within the flexible body.

23. The method of claim 21, further comprising placing the stiffening element within a sock prior to encapsulating the stiffening element in the flexible body.

24. The method of claim 21, further comprising forming a lumen within the flexible body and encapsulating the stiffening element within the lumen.

25. The method of claim 24, in which forming the lumen comprises:
placing a removable core pin into the channel;
forming a second portion of the flexible body around the removable core pin; and
removing the removable core pin from the flexible body.

26. The method of claim 21, in which the stiffening element is positioned within the cochlear lead such that the stiffening element extends from a cochleostomy approximately 8 to 9 millimeters into the cochlea when the cochlear lead is fully inserted, the stiffening element extending through the cochlear lead to approximately 11 to 12 millimeters from the distal tip of the cochlear lead; the distal portion of the stiffening element having a length of approximately 5 to 6 millimeters.

27. A method comprising:
inserting a cochlear lead with an encapsulated stiffening element into a cochlea such that the stiffening element enters a curved portion of the cochlea, the stiffening element being configured to prevent buckling of the cochlear lead and redirect an axial insertion force into a tangential force; and
continuing to insert the cochlear lead into the cochlea such that the stiffening element extends at least 180 degrees into the cochlea and is plastically deformed in a shape which corresponds to the interior of the cochlea.

* * * * *